(12) United States Patent
Kucharczyk et al.

(10) Patent No.: US 6,626,902 B1
(45) Date of Patent: Sep. 30, 2003

(54) MULTI-PROBE SYSTEM

(75) Inventors: John Kucharczyk, Minneapolis, MN (US); George T. Gillies, Charlottesville, VA (US)

(73) Assignees: University of Virginia Patent Foundation, Charlottesville, VA (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/548,110

(22) Filed: Apr. 12, 2000

(51) Int. Cl.[7] .............................................. A61B 18/18
(52) U.S. Cl. ........................................ 606/41; 606/34
(58) Field of Search .................... 606/32, 34, 41, 606/45, 49–50; 607/98–99, 101; 604/19, 21, 48, 43

(56) References Cited

U.S. PATENT DOCUMENTS

| | | | |
|---|---|---|---|
| 3,995,623 A | 12/1976 | Blake et al. ............ 128/2.06 E |
| 4,407,304 A | 10/1983 | Liber et al. ................. 128/786 |
| 5,443,074 A | 8/1995 | Roelandt et al. ............. 128/713 |
| 5,713,858 A | 2/1998 | Heruth et al. .................. 604/93 |
| 5,713,923 A | 2/1998 | Ward et al. ..................... 607/3 |
| 5,728,079 A | 3/1998 | Weber et al. ................ 604/280 |
| 5,819,737 A | 10/1998 | Young et al. ............. 128/653.2 |
| 5,865,744 A | 2/1999 | Lemelson .................... 600/407 |
| 5,868,674 A | 2/1999 | Glowinski et al. .......... 600/410 |
| 5,873,865 A | 2/1999 | Horzewski et al. ......... 604/280 |
| 5,919,135 A | 7/1999 | Lemelson .................... 600/407 |
| 5,930,329 A | 7/1999 | Navab ..................... 378/98.12 |
| 5,941,889 A | 8/1999 | Cermak ....................... 606/130 |
| 5,951,472 A | 9/1999 | Van Vaals et al. .......... 600/411 |
| 5,964,705 A | 10/1999 | Truwit et al. ................ 600/423 |
| 6,006,127 A | 12/1999 | Van Der Brug ............. 600/427 |
| 6,019,737 A | 2/2000 | Murata ........................ 600/585 |
| 6,026,316 A | 2/2000 | Kucharczyk et al. ....... 600/420 |
| 6,177,940 B1 * | 1/2001 | Bond et al. .................. 345/352 |
| 6,198,974 B1 * | 3/2001 | Webster, Jr. ................. 607/122 |

* cited by examiner

*Primary Examiner*—Roy D. Gibson
(74) *Attorney, Agent, or Firm*—Mark A. Litman & Assoc. P.A.

(57) ABSTRACT

A multi-lumen, multi-functional catheter system comprising a plurality of axial lumens, at least one lumen supporting a functionality other than material delivery and material removal.

21 Claims, 2 Drawing Sheets

Fig. 2

MULTI-PROBE SYSTEM

BACKGROUND OF THE INVENTION

1. Field of the Invention

This invention relates to an apparatus and method for catheterization of the tissues and fluid spaces, including blood vessels, of the human body. The invention also relates to the method by which diagnostic and therapeutic agents and/or procedures may be delivered to any of those body parts or regions. In particular, the present invention relates to the design and use of a multi-lumen catheter for providing multiple, and not necessarily complimentery functions, such as sampling of the fluids within the extracellular and interstitial spaces of the brain, spinal cord, or other body tissues, concurrently with drug delivery, electrical recording/stimulating, or the delivery of any other type of therapy into the same tissues in accordance with the need for such therapies.

2. Background of the Art

Surgical procedures, especially neurosurgical procedures that involve open craniotomy, carry an intrinsically high level of risk of infection and hemorrhage. A variety of new techniques aimed at minimizing the invasiveness of interventional procedures have been introduced in the hope of reducing the surgical risk and shorten a patient's hospital stay and overall rehabilitation. Placement of probes and catheters into the brain using stereotactic and image-guided procedures provides one means of minimizing these risks. However, many types of interventional procedures, including those that require drug delivery into the brain, sometimes require either catheterization at multiple target points, or subsequent re-implantation of the catheter to optimize the therapy being delivered to the brain.

Current methods of catheterization of the parenchymal tissues of the brain make it possible to measure intracranial pressure (U.S. Pat. No. 5,107,847), deliver drugs in a rate-controlled manner (U.S. Pat. No. 5,836,935), infuse various substances into the brain (U.S. Pat. No. 5,720,720), and convey fluids out of the brain (U.S. Pat. No. 5,772,625). Very recent technological developments are now leading to intraparenchymal catheterization systems that can be positioned within the brain by magnetic stereotaxis (U.S. Pat. Nos. 5,125,888; 5,707,335; 5,779,694), that are visible under magnetic resonance (MR) imaging (U.S. patent application Ser. No. 09/131,031 and U.S. Pat. No. 6,026,316), and that contain multi-purpose electrodes (U.S. Pat. No. 5,843,093). In addition, there are several types of implantable neurostimultor devices that have been disclosed. These include those described by Otten (U.S. Pat. No. 5,344,439), Hess et al. (U.S. Pat. No. , 4,800,898), and Tarjan et al. (U.S. Pat. No. 4,549,556) as three examples thereof. However, none of the available methods of intraparenchymal catheterization can carry out multiple input-output functions at the same time with the same implanted device. With the exception of the method taught by Otten (U.S. Pat. No. 5,344, 439), an already implanted device or part of an implanted device must be withdrawn before another probe is subsequently inserted into the tissue to perform additional functions. U.S. Pat. No. 5,788,713 describes the availability of both a delivery lumen and sampling lumen on a single catheter system.

One of the significant problems with delivering drugs directly into living tissue is assuring that the drug is accurately distributed to target receptor locations. The efficacious delivery of therapeutic agents for the treatment of brain tumors or neurodegenerative diseases, as two examples, requires that the agents be delivered as close to their receptors in the brain as possible, while minimizing increases in intracranial pressure during and after drug delivery. Liquid drug agents delivered into the brain through implanted catheters will disperse from the site of injection at variable rates depending on a number of factors, including the physicochemical characteristics of the drug, capillary uptake, metabolic degradation and excretion of the drug, size of the extracellular space, geometry of the brain cell microenvironment and input flow-rate and line pressure of the infusion system or other device that is pumping the drug into the brain. The degree to which each of these factors influences the distribution of a particular drug agent may be an important determinant of the effectiveness of drug treatment of diseases of the central nervous system. Additionally, the inventors have determined that it is increasingly important to determine other local characteristics of the region where active materials are delivered that can effect the efficacy or optimization of the treatment, such as pH, osmololity, viscosity, electrolyte content, temperature, fluid flow rates, and concentrations of specific ingredients. No present systems enable both the delivery of therapeutic materials and the measurement of significant local properties (except for the single noted instance of delivery and physical sampling).

Ideally, the injected, infused, or retroprofused material (e.g., a material that is "biologically active," that is a material which influences, increases, decreases or supplements biological activities on the cellular or macro-organ level, such activities, for example, including any chemical production, cell reproduction, hormone production, enzyme production, responsive activity, and the like) infiltrates the extracellular space, and the subsequent distribution of the drug within the tissues is governed mainly by its molecular weight, molecular radius, the structure and hydraulic conductivity of the tissue matrix into which the material has been injected, and the hydrodynamics of the infusion process. However, various flow scenarios may lead to tissue swelling, an increase in ICP (intracranial pressure) and, secondarily, altered interstitial transport of the drug solute.

Invasive ICP devices have generally evolved in two basic directions. The first is based on implanting a sensor within the cranium. The second is based on mounting the sensor externally and connecting the measurement site through a fluid-filled transmission line. The three main sites for ICP monitoring are the lateral ventricle, the extradural space, and the subdural or subarachmoid spaces.

U.S. Pat. No. 4,014,319 to Favre discloses an intracranial pressure transducer comprising a small sealed capsule positioned in a trephined hole in the patient's skull, wherein a sensor diaphragm in contact with the dura mater is displaced by changes in intracranial pressure and produces an output signal proportional to the change in intracranial pressure. U.S. Pat. No. 4,026,276 to Chubbuck discloses a pressure monitoring apparatus implantable in the cranium, wherein the apparatus comprises a passive resonant circuit with inductance and capacitance capability for measuring intracranial pressure by comparison to a reference ambient pressure. U.S. Pat. No. 4,062,354 to Taylor, et al. discloses an intracranial pressure transducer system comprising a holding bracket containing sensor elements which is positioned against the dura of the brain, wherein the elements within the holding bracket transmit electromagnetic signals related to the intracranial pressure to a receiver outside the patient's body. U.S. Pat. No. 4,080,653 to Barnes, et al. discloses a method and apparatus for recording intracranial pressure utilizing a transducer amplifier. U.S. Pat. No. 4,114,603 discloses an intracranial pressure monitoring device comprising a pressure-sensitive catheter insertable between the dura mater and arachnoid membrane.

U.S. Pat. No. 4,114,606 discloses a monitoring apparatus for intracranial pressure measurement, wherein electromagnetic radiation is imposed on a passive circuit implanted in the cranium, the frequency at which the radiation is absorbed reflecting intracranial pressure. U.S. Pat. No. 4,147,161 to Ikebe, et al. discloses a system for measuring or monitoring intracranial pressure which comprises a non-elastic detecting pouch inserted between the skull and the brain, wherein a pressure measuring device in the liquid in the pouch indirectly measures the intracranial pressure. U.S. Pat. No. 4,156,422 to Hildebrandt discloses an apparatus for treating hydrocephalus comprising a housing which contains subcutaneously implantable components for measuring and controlling fluid pressure, wherein a second housing outside the patient contains measuring and control components whereby an intracerebral space may be automatically drained in response to a predetermined adjustable ICP.

U.S. Pat. No. 4,210,029 to Porter discloses a differential sensor unit utilizing fiber optic light guides, wherein three light guides pass within a pneumatic line into one end of a rigid cylindrical envelope implanted in the skull. Detectors are arranged to actuate pressure display and pneumatic controls to adjust the internal pressure of the envelope to match the ICP and thereby measure the ICP. U.S. Pat. No. 4,265,252 to Chubbuck discloses an implantable transensor device containing a passive RF resonant circuit which is responsive to changes in ICP. U.S. Pat. No. 4,385,636 to Cosman discloses an implantable telemetric differential pressure sensing device comprising a planar closed conductive loop which moves with a flexible diaphragm, wherein the resonant frequency of the conductive loop is detected telemetrically to determine pressure in a body compartment.

U.S. Pat. No. 4,340,038 to McKean discloses a magnetic field generator and magnetic pick-up coil contained in an implanted ICP monitoring device. U.S. Pat. No. 4,354,506 to Sakaguchi, et al. discloses an intracranial pressure gauge which comprises a powerless resonance circuit composed of a coil and a condenser, a sensor equipped with an implantable pressure-sensitive section capable of changing the inductance or the capacitance of the condenser in response to a change in ICP. U.S. Pat. No. 4,438,773 to Letterio discloses an implantable subarachnoid bolt for use in measuring ICP.

U.S. Pat. No. 4,465,075 to Swartz discloses an integrated circuit including a pressure transducer and temperature compensation circuit. U.S. Pat. No. 4,471,786 to Inagaki discloses a telemetering intracranial pressure transducer for detecting ICP, wherein a pressure-receiving layer disposed in contact with the dura mater transmits an output signal to a telemetering transmission circuit housed entirely beneath the patient's scalp. U.S. Pat. No. 4,600,013 to Landy, et al. discloses a probe for ICP measurements in the subarachnoid space, said probe comprising a threaded shaft having a lumen in contact with a pressure transducer. U.S. Pat. No. 4,621,647 to Loveland discloses an apparatus for monitoring and regulating ICP, wherein a manometer, transducer and regulator are interconnected by tubing and stopcocks.

U.S. Pat. No. 4,627,443 to Chubbuck, et al. discloses an X-ray readable implantable pressure sensor, wherein shifting of a radiopaque means is observed to indicate the change in pressure of a body cavity. U.S. Pat. No. 4,677,985 to Bro, et al. discloses an intracranial probe to monitor both ICP and blood flow by thermal diffusion and hydrogen clearance techniques. U.S. Pat. No. 4,703,757 to Cohen discloses an optical fiber pressure transducer, wherein variations in transversely applied pressure to an elongated flexible fiber results in proportional light refraction and corresponding output signal.

U.S. Pat. No. 4,711,246 to Alderson discloses a miniaturized pressure transducer, wherein light transmitted through a single optical fiber is reflected by a diaphragm in accordance with the pressure being measured. U.S. Pat. No. 4,723,556 to Sussman discloses an intracranial ventricular catheter assembly, wherein a pressure sensing device is connected to the proximal catheter. U.S. Pat. No. 4,738,267 to Lazorthes, et al. discloses an implantable intracranial pressure sensor, wherein a pressure-sensitive diaphragm placed directly on the dura mater transmits the intracranial pressure through a resistive type transducer.

U.S. Pat. No. 4,772,257 to Hakim, et al. discloses an external programmer for magnetically-adjustable cerebrospinal fluid shunt valve. U.S. Pat. No. 4,858,619 to Toth discloses an intracranial pressure monitoring system, wherein relief valves are combined with a pressure sensor for automatic venting of cerebrospinal fluid during elevated ICP. U.S. Pat. No. 4,805,634 to Ullrich, et al. discloses an adapter assembly for accurately positioning a removeable biosensor implanted in the cranium. U.S. Pat. No. 4,841,986 to Marchbanks discloses a method and apparatus for measuring ICP, wherein a pressure sensor placed against the eardrum indirectly detects ICP changes based on displacement of the eardrum.

U.S. Pat. No. 4,903,707 to Knute, et al. discloses a ventricular catheter assembly comprising a catheter and a bolt, wherein the catheter can be inserted to a predetermined depth into the cranium. U.S. Pat. No. 4,995,401 to Bunegin, et al. discloses a device for measuring anterior fontanelle pressure, wherein ICP changes can be detected noninvasively. U.S. Pat. No. 5,000,049 to Cooper, et al. discloses an apparatus for measuring fluid pressures using a catheter device. U.S. Pat. No. 5,005,584 to Little discloses a fiber optic transducer utilizing a flexible membrane to transduce pressure by interrupting light transmission between fiber optic paths in a catheter or guide wire carrier.

U.S. Pat. Nos. 5,074,310 and 5,117,835 to Mick disclose a method and apparatus for non-invasively measuring changes in ICP, wherein a predetermined vibration signal is applied to one location in the skull and an output vibration signal is detected from another location in the skull, reflecting ICP changes over time. U.S. Pat. No. 5,108,364 to Takezawa, et al. discloses a monitoring catheter for medical use comprised of multiple tubes equipped for fluid delivery and removal, pressure measurement, and temperature measurement. U.S. Pat. No. 5,113,868 to Wise at al discloses a pressure sensing catheter system comprising a catheter, a pressure sensor, and a signal conduit means within the catheter for signals between an external monitor and the pressure sensor, the signal conduit including two electrical conductors which are connectable to the external monitor. U.S. Pat. No. 5,191,898 to Millar discloses a cerebroventricular catheter means of measuring ICP and injecting or withdrawing cerebrospinal fluid, wherein a transducer positioned at the end of the cerebroventricular catheter and electrically coupled to a monitor allows for ICP monitoring.

Guidewires for the catheter or drug delivery system are usually made of radiopaque material so that their precise location can be identified during a surgical procedure through fluoroscopic viewing. Exemplary of guidewires used under X-ray viewing is the guidewire disclosed by LeVeen, U.S. Pat. No. 4,448,195, in which a radiopaque wire can be identified on fluoroscopic images by metered bands placed at predetermined locations. The U.S. Pat. No. 4,922,924, awarded to Gambale et al. discloses a bifilar arrangement whereby radiopaque and radiotransparent filaments are wrapped on a mandril to form a bifilar coil which provides radiopaque and radiotransparent areas on the guide wire. U.S. Pat. No. 5,375,596 to Twiss et al. discloses a method for locating catheters and other tubular medical devices implanted in the human body using an integrated system of wire transmitters and receivers. U.S. Pat. No. 4,572,198 to Codrington also provides for conductive elements, such as electrode wires, for systematically disturbing the magnetic field in a defined portion of a catheter to yield increased MR visibility of that region of the catheter. However, the presence of conductive elements in the catheter also introduces increased electronic noise and the possibility of Ohmic heating, and these factors have the overall effect of degrading the quality of the MR image and raising concerns about patient safety. Thus, in all of these examples of implantable medical probes, the presence of MR-incompatible wire materials causes large imaging artifacts. The lack of clinically adequate MR visibility and/or imaging artifact contamination caused by the device is also a problem for most commercially available catheters, microcatheters and shunts. MRI enables image-guided placement of a catheter or other drug delivery device at targeted intracranial loci. High-resolution visual images denoting the actual position of the drug delivery device within the brain would be extremely useful to the clinician in maximizing the safety and efficacy of the procedure. Drug delivery devices, such as catheters, that are both MR-visible and radio-opaque could be monitored by both X-ray fluoroscopy and MR imaging, thus making intra-operative verification of catheter location possible.

U.S. Pat. No. 5,291,899 to Watanabe, et al. discloses a method for measuring ICP by using a device comprising a reservoir implantable under the skin of a patient and into which cerebrospinal fluid can be introduced from the ventricle of the patient, a flexible dome configured to be upwardly projected from said reservoir by the pressure of the cerebrospinal fluid and flexibly deformable according to an external force, a pressing part for pressing against said dome through the skin, a pressing-part-driving means for driving said pressing part pressing the dome and a flexible membrane provided at the tip of the pressing part and having an interior filled with a fluid, the method comprising: pressing the flexible membrane of the pressing part against the dome of the reservoir through the skin by means of the pressing-part-driving means after a zero point correction of the pressure transducer is performed by communicating the interior of the flexible membrane with the atmosphere.

U.S. Pat. No. 5,325,865 to Beckman, et al. discloses a catheter assembly for measuring fluid pressure in a body cavity, comprising an optical converter responsive to an electrical power source for energizing a light-emitting diode which has drift characteristics which vary in response to temperature, and a detection circuit.

U.S. Pat. No. 5,230,338 to Allen, et al. discloses an interactive image-guided system for displaying images corresponding to the placement of a surgical probe in the body. U.S. Pat. No. 4,173,228 to Van Steenwyk, et al, and U.S. Pat. No. 5,042,486 to Pfeiler, et al. disclose medical probes wherein electromagnetic signals are propagated between one antenna on the tip of the probe inserted into a body region and several antennae outside the body. The position and orientation of the probe tip are determined from the signals transmitted between said antennae. U.S. Pat. Nos. 5,211,165 to Dumoulin, et al, U.S. Pat. No. 5,255,680 to Darrow and Dumoulin, U.S. Pat. No. 5,307,808 to Dumoulin, et al., and U.S. Pat. No. 5,318,025 to Dumoulin, et al. additionally disclose a tracking system in which radiofrequency signals emitted by an invasive device, such as a catheter, are detected and used to measure the device's position and orientation in a patient. Localization of a device in situ is achieved by transmit radiofrequency coils positioned at its distal end, which are detected by receive radiofrequency coils positioned around the imaging volume of interest. The position of the device, as determined by the tracking system, is superimposed upon independently acquired diagnostic images. U.S. Pat. No. 5,383,454 to Bucholz discloses a system for indicating a position of a tip of a probe which is positioned within an object on images of the object, wherein a computer employing translational software translates the position of the tip of said probe into a coordinate system corresponding to the coordinate system of the cross-sectional images.

Each of the above-cited patents provide advantages and disadvantages for monitoring of ICP and other tissue parameters related to intracranial drug delivery. For instance, intraventricular catheters are accurate but may be difficult to position in the presence of brain swelling and shift. Subarachnoid devices are easily placed but may underestimate higher ICP pressures, particularly if they are not coplanar to the brain surface. Epidural devices require placement through a burr hole and can be hampered by recording artifacts, damping, and problems with calibration. (We note that Raabe and colleagues have published an article in Neurosurgery, Vol. 42, No. 1, pps. 74–80, 1998, that discusses techniques that attempt to avoid certain methodological errors that arise in the use of some ICP measurement devices.) Moreover, none of the above cited patents disclose a method and means for evaluating changes in ICP resulting from the direct injection or infusion of drug agents into brain tissues as does the present invention.

U.S. Pat. No. 5,843,093 to Howard discloses a dual purpose neuron-monitoring electrode assembly particularly suited for performing magnetic pallidotomy for the treatment of Parkinson's disease. However, unlike the present invention, the patent to Howard does not provide for an MR-compatible, multi-lumen probe which is capable of containing several different internal devices that can sample the extracellular environment and react to it.

U.S. Pat. No. 5,843,150 to Dreessen, et al. discloses a system and method for providing electrical and/or fluid treatment within a patient's brain, wherein the device is an implantable device comprising a lumen, a catheter, an electrode, and a pump. However, unlike the present invention, the patent to Dreessen, et al. does not provide for an MR-compatible, multi-lumen probe which is capable of containing several different internal devices that can sample the extracellular environment and react to it.

U.S. Pat. No. 5,861,019 to Sun, et al. discloses a telemetry system for communications between an external programmer and an implantable medical device. However, unlike the present invention, the patent to Sun, et al. does not provide for an MR-compatible, multi-lumen probe which is capable of containing several different internal devices that can sample the extracellular environment and react to it.

U.S. Pat. No. 5,843,148 to Gijsbers, et al. discloses a brain stimulation lead and multiple electrodes for precise delivery of electrical stimuli to a patient's brain. However, unlike the present invention, the patent to Gijsbers, et al. does not provide for an MR-compatible, multi-lumen probe which is capable of containing several different internal devices that can sample the extracellular environment and react to it.

U.S. Pat. No. 5,820,589 to Torgerson, et al. discloses an implantable medical pump comprising a fluid reservoir, a passive regulator assembly, an electromechanical controls means, and a means for receiving radio frequency signals to operate the electromechanical control means. However, unlike the present invention, the patent to Torgerson, et al. does not provide for an MR-compatible, multi-lumen probe which is capable of containing several different internal devices that can sample the extracellular environment and react to it.

U.S. Pat. No. 5,821,011 to Taylor, et al. discloses a device for implantation in a human body in contact with body fluids, which includes an electrical terminal, a glass insulator, and a sleeve positioned between the glass insulator and a container. However, unlike the present invention, the patent to Taylor, et al. does not provide for an MR-compatible, multi-lumen probe which is capable of containing several different internal devices that can sample the extracellular environment and react to it.

U.S. Pat. No. 5,826,576 to West discloses an electrophysiology catheter which includes a handle, a catheter shaft with a flexible tip portion with one or more electrodes, a multi-function wire extending along the catheter shaft, and one or more micromanipulators. However, unlike the present invention, the patent to West does not provide for an MR-compatible, multi-lumen probe which is capable of containing several different internal devices that can sample the extracellular environment and react to it.

U.S. Pat. No. 5,858,009 to Jonkman discloses a multi-lumen cannula for conducting fluid to and from a body region, especially in left-heart and right-heart assist cardiac surgical procedures, wherein the septum separating the first and second catheter lumens is wire-reinforced to resist deflection of the septum.

PCT application WO9807367A1 to Jolecz, et al. discloses image-guided means and apparatus for ultrasound delivery of compounds through the blood-brain barrier to selected locations in the brain.

SUMMARY OF THE INVENTION

A multi-lumen catheter system with novel forms and functions is disclosed. A desirable design feature for practice of this invention comprises an elongate element, such as a central barrel of a catheter which is surrounded by (or including within a major lumen) additional lumens which perform or transport various functions. In one embodiment that is particularly useful for therapy of the parenchymal tissues of the brain, one or more of the plurality of lumens around the central barrel are configured for sampling of fluids within the interstitial space (e.g., semiconductor based, microdialysis-based, electronically based, electrically based, interactance and transmittal, etc. sampling). Other lumens of the multi-lumen probe can be used for the delivery of drugs, therapeutic agents, diagnostic agents or view-enhancing agents into the parenchymal tissues, either via efflux from a single drug delivery lumen or via a multi-port configuration to facilitate broad spatial distribution of the drug within the tissue. In this embodiment, the central lumen can be used for any treatment or function, but especially either microdialysis or drug delivery, or it can be configured to accommodate a recording or stimulating electrode, such as a multi-purpose stereotactically placed electrode (e.g., U.S. Pat. No. 5,843,093). In a method of the invention, additional probes or devices that might be passed through either the central barrel of the catheter or through one of the surrounding ports include intracranial pressure probes, optical fibers and/or optical fiber bundles configured for conveying illumination and/or optical signals to and from the target tissues, iontophoresis probes, thermometry probes, blood-flow-sensing probes, chemical probes, sensing devices (even audio sensing devices, pressure-sensing devices, pH sensing devices, viscosity or osmololity sensing devices, radiation-sensing device, light-sensing device, etc.), vacuum lines, fluid delivery tubes and conduits, guidewires, fixed and adjustable-tipped steering probes and wires, electric field and magnetic field-sensing probes, electrodes and applicators, gene analysis chips and "lab-on-a-chip" structures, biopsy devices, tissue and cell implantation devices, cryogenic probes, thermal probes, ablation probes, cauterizing probes and tips, stents, coils, angioplasty balloons and devices, radioactive sources, magnetic and electric field sources, integrated circuits and electronic devices.

The unique compound nature of the catheter which is the subject of the present invention makes it possible to carry out several diagnostic and therapeutic tasks concurrently, with or without additional functional coupling between the processes. An important attribute of the medical device disclosed by this invention is to optimize the therapeutic response to the patient's clinical condition by using the sampling capabilities of the microdialysis or other diagnostic components of the catheter to provide information on the metabolic state of the target tissue (especially the brain) via analysis of the fluids within the extra-cellular matrix. Drug delivery into the parenchymal tissues can then be carried out via positive pressure infusion, or by diffusion-based delivery of pharmacological agents via the microdialysis process, using available lumens within the catheter to carry out either form of treatment. In parallel with drug delivery, electro-stimulation of the same or nearby target tissues/neurons can be carried out via a recording/stimulating electrode passed down a central or radially disposed barrel of the device.

In a method of the invention, a feedback mechanism may be used to automate and optimize the entire process, wherein a number of physiological variables can be taken into account by an algorithm that governs the therapeutic response of the catheter system. In another embodiment, physiological and metabolic data on the status of the patient (derived form other sensors on/in the body, such as, for example, probes which monitor tissue oxygen levels, blood pH, concentration of materials in the blood, blood flow, and other physiologic parameters) can be incorporated into the algorithm's treatment optimization process. Thus, for example, if a stroke or brain-injury patient were in an intensive care unit or other hospital bed setting, the vital-signs data from patient monitoring systems (including, in particular, intracranial pressure measurements) could be monitored by the system's signal processor, wherein the resulting information provided feedback control of the rates of drug flow into the brain. In another embodiment of the method of the invention, the microdialysis systems of the catheter device are used to sample endorphin levels, wherein the catheter's signal processor could then provide feedback control of the electrostimulation process so as to attenuate the effects of chronic pain.

In another embodiment of the method of the invention, the algorithm governing the patient's therapy preferably utilizes proportional-integral-derivative (PID) control functions, adaptive control functions, nonlinear control functions, multi-variable/state-space control functions, stochastic control functions and/or any other functional approach deemed appropriate for the implementation of the therapy. In all such cases, the controller could be designed to respond to changes in the patient's condition using artificial intelligence techniques that would let the feedback mechanism "learn" the best way to respond to changes in the patient's physiological or anatomical status. Such techniques might employ, among other things, "fuzzy logic" algorithms that can function in the presence of incomplete or indeterminate data.

A summary of the present invention includes at least a multi-lumen, multi-functional catheter system comprising a plurality of axial lumens, at least one lumen supporting a functionality other than material delivery and material removal. At least two individual lumens may be parallel to a central barrel of the catheter, and at least one of the at least two lumens may be used for sampling fluids in a body part into which the catheter is inserted. At least one of the axial lumens may be used for infusion, injection or other mechanism of delivery of diagnostic and/or therapeutic agents into a body part in which the catheter is inserted. The central lumen of the catheter may contain an electrode, such as a neurostimulator or radiofrequency-ablation lead. An outer surface of the catheter may comprise a continuous sheath inside of which are located individual lumens, a central barrel and other functional components of the catheter system. At least some of said other function components may comprise electrical leads. There does not have to be an envelope around the catheter system, so there need not be any exterior covering element over the at least two lumens, a central barrel and other functional components of the catheter system. It is expected that at least one biological or physiological measuring device is present within at least one lumen. Such a biological or physiological measuring device would be expected to be connected to a signal receiving device by an electrical lead associated with the catheter system. The at least one biological or physiological measuring device may connected to a signal receiving device by an electrical lead permanently attached to the catheter system. The at least one diagnostic component may provide any useful information, such as information about metabolic, physiologic and/or anatomic status of a patient. The information from said at least one biological or physiological measuring device would ordinarily be received by a host computer connected to said device. More than one component or sensing element or measuring device would be among components that provides information other than information from said at least one biological or physiological measuring device. All or most of that information should be received by a host computer to evaluate a treatment procedure or patient conditions around the locality of treatment. The additional components may measure, for example, vital signs of a patient. Information from more than one information source may received by the host computer and a treatment planning and control algorithm could be present in said host computer to process that information from more than one source.

A method according to the invention for treating a patient according to a treatment plan could comprise inserting the catheter system the invention into a patient, delivering therapy to the patient through at least one lumen of said catheter system, taking biological or physiological measurements of tissue or fluids within the patient, reporting said information to a computer, and evaluating performance of the treatment plan with the computer based upon comparing said information to expected biological or physiological information. The method could include information relating to at least two different biological or physiological measurements being electrically transmitted to the computer for evaluating performance of the treatment plan. Upon evaluation of the performance of the treatment plan, the computer could indicate a) a deviation for a range of acceptable levels of performance of the treatment plan, and b) an alteration of an existing treatment plan is identified. The method could have the computer signal the catheter system to actively modify the existing treatment plan. The method could also include having the computer signal an operator to actively modify the existing treatment plan.

DETAILED DESCRIPTION OF THE INVENTION

The present invention has enabled the combination of multiple functions into a catheter or probe system, enabling the performance of complete procedures by catheter along with additional, multiple or complete capability for ancillary or essential analytical procedures, diagnostic procedures, quantitative and qualitative analyses, operational environmental determinations, and any other task or information providing mechanism that provides information useful to the operation procedure. For example, a catheter system according to the present invention may provide two, three, four or more separate and distinct functions that can be performed distally (at the site of the catheter) without the necessity for removal of distal elements or replacement of the catheter. Information from the distal location can then be transmitted to a proximal intelligence source (e.g., processor, microprocessor, computer, hardware, software, etc.) for reading, visualization, analyzing, comparing, evaluation, and the like. This information can then be used to evaluate the ongoing procedure on a periodic, episodic, near real time, or real time basis to suggestion continuation of the existing procedure or alteration of the procedure. For example, the catheter may have separate biological and physiological delivery and evaluation systems for in vivo activity during a procedure. This can be important as ambient or induced biological activity and ambient or induced physiological activity can have direct results on the efficacy of the treatment or may indicate problems with the procedure. Determination of the status of these activities can assist in the assurance that an optimal or satisfactory procedure is being performed, and suggest methodology on improving the procedure while it is being administered. Multiple procedures or ancillary procedures, and multiple forms of operation environment evaluations can be performed through a single catheter with a single insertion of a catheter, with many or all of the functional elements needed for the procedures originally delivered with the catheter insertion or fed through the catheter. For example, tissue can be removed from a surface, therapeutic material delivered to the site, and conditions monitored on a local level to assure that at least minimal performance or operation standards are being maintained within the operational environment. A prophetic example of a multiple function procedure supported by a catheter according to techniques of the invention would be treatment of an area of tissue in the cranium where infection has damaged tissue over a targetable surface area. A catheter would be designed to provide fiber optic viewing capability with a multiplicity of fiber optic viewing fibers (and an optional light piping fiber), an ablative or irrigating device to remove irreparably damaged surface tissue, a removal lumen would be provided to assist in the physical removal of detritus from the removed damaged tissue, a delivery lumen would provide therapeutic agent to assist in the rapid healing or protection of newly exposed tissue that had previously been under the damaged tissue, and a solid state (e.g., semiconductor) pH sensing element extending from its own lumen can assist in measuring real time pH in the region of the therapeutic material delivery to assure that the pH in the region does not vary to such a degree that would indicate some deviation from the desired rate of delivery or loss of fluid from the newly exposed tissue. Other sensing systems (e.g., pressure measuring, thermometric, chemometric, etc.) can also be present. These sensing systems would transmit electrical signals through conductive elements (e.g., lines, wires, coils, etc.) to reading or recording systems. This information, either directly from the electrical conductors or through the reading or recording systems, would be evaluated (either by an operator or by artificial intelligence) and the procedure evaluated (by an operator or computer) on the basis of the information provided. The evaluation, based on known parameters for measuring the compliance of the procedure to acceptable standards, would dictate or indicate continuation of the procedure, modification of the procedure, or cessation of the procedure.

Evaluation of the performance of the procedure by artificial intelligence (e.g., hardware, software, computer, processor, microprocessor, chips, circuit boards, and the like) can be performed by any acceptable format. Specific or modified programs (for individual patients, for ranges or parameters within operable conditions, or specifically identified conditions being treated) can be provided to the artificial intelligence that suggest or dictate the progression of the procedure depending upon the readings. Although some general programs for the procedures my be developed, the system is particularly useful for increased automation of procedures where unusual circumstances might be present, such as patients with particular toxicity sensitivities, patients with underlying conditions (e.g., Parkinsonism, Type I diabetes, alcoholism, drug dependency, PKU, allergies, and the like) or patients on separate drug therapies where changed conditions in their blood chemistry from the operational procedure could affect the underlying condition. The software for the operational procedure could include special commands and attributes for the unique conditions or patients undergoing the procedure. As local conditions that could contribute to complications in operations are presently not easily considered and measured on a real time basis, this type of procedure, and especially tailoring the software to procedures on patients with unique requirements provides a significant advance within the field. As an example of this, the pH level of patients suffering from long term drug dependency (including excessive alcohol use) may have blood pH levels that are not within a normally accepted range. As some drugs and therapies may have pH sensitivities themselves, and the therapy may itself alter local pH even further, special modifications in the rates and/or concentrations of delivery may have to be modified in the program for a particular patient. A standard software procedure for otherwise healthy patients would not consider this underlying condition, even to the extent that a modification suggested by the 'normal' program could worsen the procedure under the special conditions of the underlying condition.

Figure 1:
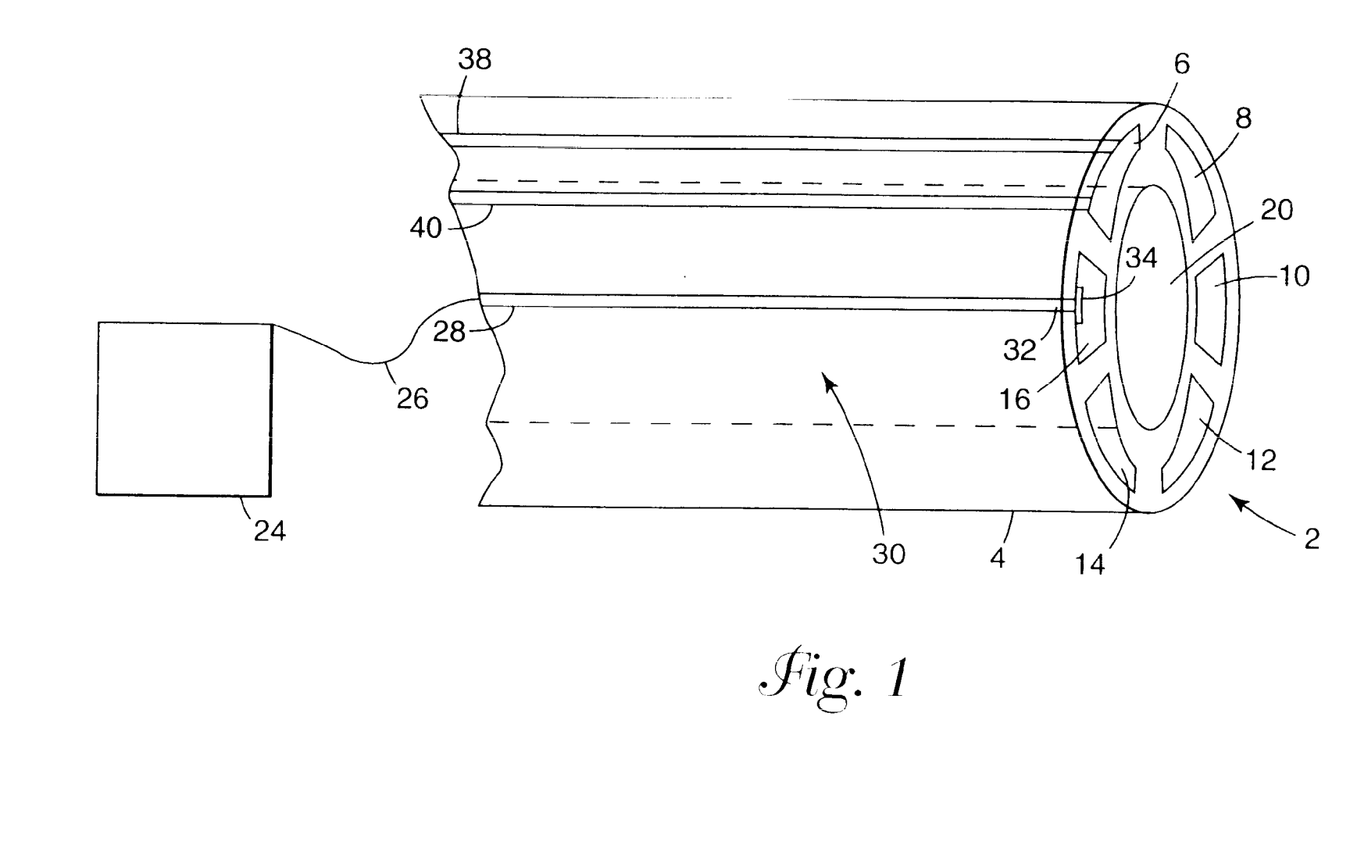
FIG. 1 is a representation of a layout of one embodiment of a multi-lumen, multi-function catheter system disclosed by the present invention.

FIG. 1 is a representation of a layout of one embodiment of a multi-lumen, multi-function catheter system disclosed as an aspect of the present invention. The catheter superstructure or manifold 2 comprises an external guide-tube 4 that contains the six individual internal lumens 6, 8, 10, 12, 14 and 16 of the catheter, or of a skeleton-like framework (shaped in cross section like a star washer) to which are affixed the individual lumens, including the central barrel 20 of the catheter. (Some specific configurations of the assembly of lumens that formulate the catheter are described later in FIG. 2.) There may be several such individual lumens (for instance, up to "n" of the type of internal lumens such as 6, 8, 10, 12, 14 and 16) inside of or otherwise integral to (e.g., distinct, self-supporting extruded tubes carried on an exterior surface or interior surface) the overall device. Some of the internal lumens can be configured as microdialysis devices, e.g., designed to sample the interstitial fluids. Other internal lumens might be infusion probes or drug delivery membranes. An online, real-time assessment of the dialysates gathered by such microdialysis devices can be accomplished by a variety of methods and systems that might range from microscale liquid chromatograph systems that are part of the physical structure of the device, to sophisticated, stand-alone genetic material analyzers and processors. Concurrently with the microdialysis analyses, a data acquisition system 24 can be added when needed to read in obtained and transmitted signals. The signals may be transported to the data acquisition system 24, for example, through a lead wire 26. That lead wire 26 is connected to a conductive element 28 embedded or affixed to the surface 30 of the guide tube 4. The conductive element 30 is electrically connected at a distal end 32 to a contact plate 34. The contact plate 34 is provided so that any functional device or microcatheter (not shown) can be electrically connected to the data acquisition system 24 easily, merely by being in electrical contact with the contact plate 34. In this manner, a multi-probe component (a component catheter) of the system could be produced as a catheter, and a selection of electrically driven or signaling elements may be inserted into the component catheter. Snaps and other securing fitting may be provided, and these snaps and fittings may themselves be remotely controlled to secure and then release specific lumen fed devices on the catheter. Where there are both active and signaling functions within a single lumen (as in 6), there may be multiple electrical leads 38 and 40. There may be three, four or more electrical leads at each lumen, as is needed. These electrical leads may be manufactured by any convenient manner such as microlithographic etching of a metal coating into a circuit or conductor pattern, extruding conductors along with the extrusion of the guide tube 4, and the like. The availability of multiple electrical leads 38 and 40 allows for the possibility of systems wherein at a single lumen, a device may be secured, released, activated, signaled to, signaled from, and programmed (if it contains memory). This offers unique functional capability to the system and the ability of the operator to control the local events of a procedure.

Figure 2:
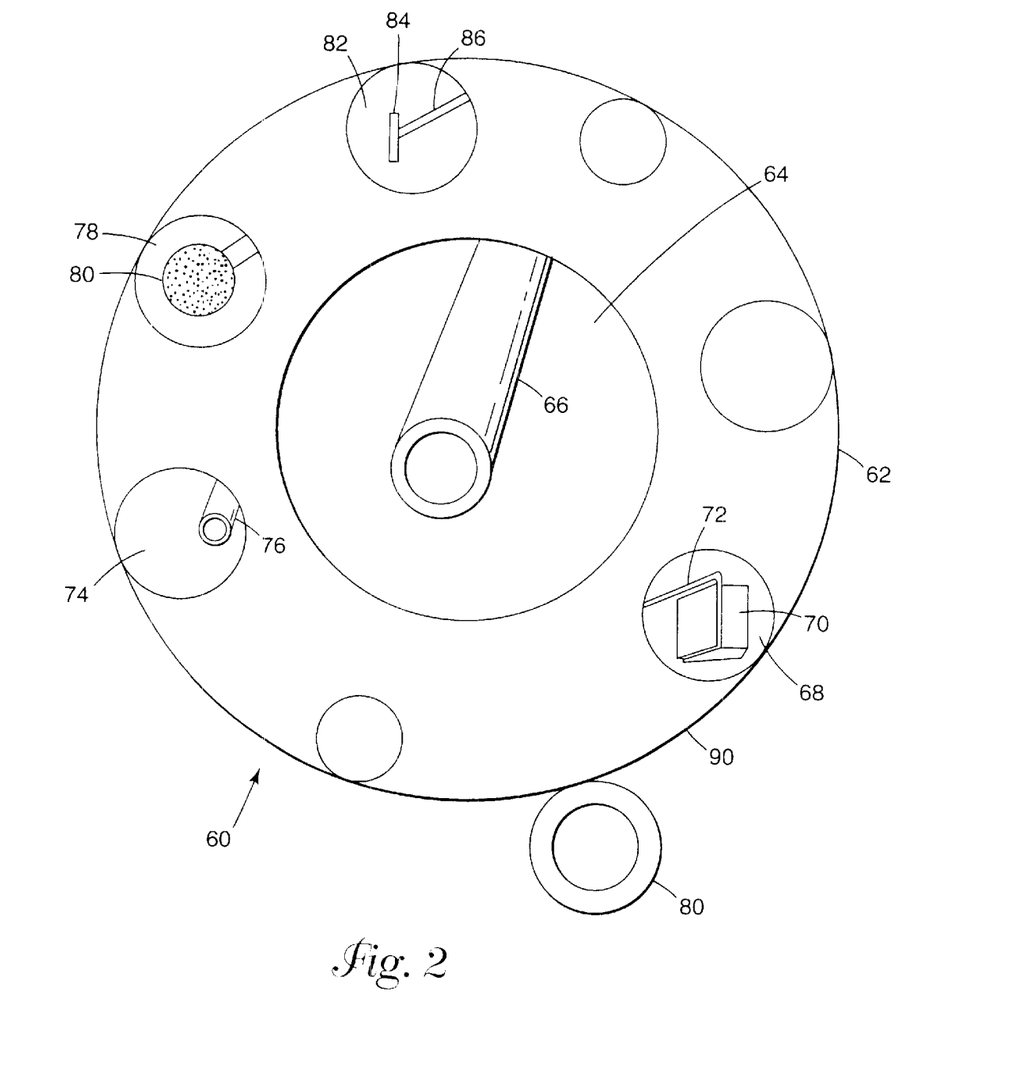
FIG. 2 shows a cross-sectional view of one embodiment of a multi-lumen catheter device.

FIG. 2 shows a cross-section of a multi-probe catheter 60 of the invention. A central barrel 64 is shown carrying a microcatheter 66 that can deliver material within a patient. Lumen 68 is shown carrying a solid state sensor 70 with an electrical conductor 72 carrying away signals. Another lumen 74 is shown carrying away a sampling tube 76. A third lumen 78 is shown carrying an abrading tip 80 that may be distally or remotely controlled. A fourth lumen 82 carries a pH sensor 84 which is electrically connected to a conductor or wire 86 that carries signals from the pH sensor 84 to a computer (not shown). It is to be noted that lumens may be of different diameters, unevenly distributed, and as with lumen 88, may be located outside of the main surface 90 of the catheter 60.

The lumens, or at least some of the lumens, may carry vital signs sensors (e.g., pH sensors, pulse sensors, electrolyte concentration sensors, pressure sensors, specific solute sensors and any other type of medical monitors) that might be needed or desirable to successfully treat the patient. The data collection acquisition device 24 (e.g., a host computer) may collect and process these data via a treatment planning algorithm that the patient's physician deems appropriate for the therapy being given, such as, for example the delivery of electrostimulation via a probe (not shown) through lumen 8 within the central barrel 20 of the catheter 2. The strength of the stimulation signal can be regulated by a controller upon instruction from the host computer or the computer can directly institute a modification of the procedure, particularly with coincident notification to the controller. An infusion and dialysis drug delivery controller electrically connected to the computer or manually operated can also be used to regulate the influx of drugs or other therapeutic agents into the patient via syringe drivers and infusion and output dialysis membrane probes passed through other available lumens (e.g., 10 and 12) in the catheter 2. In other embodiments of this invention, the treatment planning process might be carried out by the physician without recourse to an automated mechanism (computer, etc.). In such circumstances, the physician or therapist could simply monitor the results of the dialysis process and manually regulate the flow rates, pressures, and other variables of the infusion, dialysis drug-delivery, and electrostimulation processes. In still other embodiments of this invention, the computer and possibly other components of the therapy control system can be located at a remote site, perhaps a hospital or a care-provider's office. The input and output signals to and from the therapy control system can be mediated via transmission over wired or wireless telephone systems or by other types of data telemetry including satellite-based and other kinds of telemedicine linkages. As shown in FIG. 1, individual lumens can be made in a variety of sizes to suit the application at hand for each of them. They might also have a variety of different port structures, for microdialysis, infusion, and other therapy delivery techniques.

One embodiment of the present invention also may comprise an integrated electronic personal health care monitoring system. The personal health care system center could comprise, for example, a computer for receiving or acquiring, storing, processing, and transmitting information, and a plurality of interfacing ports. Each interfacing port is adapted to accept a plurality of different patient monitoring modules, a plurality of different accessory modules for transactions, and a plurality of other interactive modules. Each module would be electrically interconnected to the data processor via the computer's bus to exchange information with the computer's CPU. The data processor includes means for providing operating instructions to the sensor modules, accessory modules, and therapy-providing modules. Each module provides information on a condition or vital sign of the patient. The data processor monitors the information provided by the modules and would act on it via an algorithm run by the computer.

The specific design of any feedback system disclosed by the present invention will depend on the application for which it is to be used. In general, it will have the arrangement shown in FIG. 1. Dialysates sampled by the microdialysis probes will be analyzed by an online monitor, and the resulting data (following the necessary signal conditioning and, where appropriate, analog-to-digital conversion) will be input to a dedicated computer (CPU) that can also monitor the patient's vital signs, ICP readings, etc. The CPU can use any of a number of different feedback and control algorithms ("Patient Treatment Plans" or PTPs) selected by the physician as being the most appropriate for the needs of the patient at the time of treatment. Such PTPs might incorporate straightforward PID laws or any other feedback control mechanism that effectively regulates drug delivery and electrostimulation levels as needed. In the method of the invention, the CPU that processes the feedback control mechanism can be in the patient's home, at the hospital bedside, in the physician's office, or at a location remote to the patient. In the latter case, given that the data rates for most physiological processes can be made slow, it would be possible to transmit/receive information to/from the processing computer using either ground-based or cellular phone systems and a modem. Thus, in a preferred embodiment of the invention, a physician or other appropriate health care professional can monitor and adjust the therapy provided to the patient, eg., the stimulation level, drug delivery rate, etc., via a telemedicine link, rather than requiring a visit by the patient to a conventional clinical care setting.

The system may include testing and measuring instruments to monitor the patient's vital physiologic information, and may be adapted to a home healthcare and maintenance environment, even on a specific (unique) patient basis. The system may further include control devices having health care and maintenance functions monitored by the testing and measuring instruments in the system. In one embodiment wherein the system is arranged in the centralized network configuration, the testing and measuring instruments and the control devices are connected via a local area network with a data controller wherein all the vital information obtained in the system is stored. Instruments and devices are permitted controlled access to the controller through the network to retrieve necessary vital information therefrom. In another embodiment, the system is arranged in the distributed network configuration, with the vital information obtained by respective measuring instruments stored therein.

FIG. 2 shows two examples of cross-sectional views of an actual multi-lumen multi-function catheter device. Each of the lumens has nominally the same internal diameter, although they can be of different internal diameters, as dictated by design considerations. The central barrel 52 of the catheter contains an electrostimulation lead 50 centered within it. The structural elements 53 keep the individual internal lumens 54, 56, 58, and 60 and the central barrel from collapsing upon each other during catheter insertion, withdrawal, or during use.

These techniques may be used alone or in combination with the techniques described in U.S. Pat. No. 6,026,316 wherein problems, such as the following are addressed by real time or near real time observation of material concentration changes are observed by MR imaging techniques and acted upon after observation. One of the significant difficulties with delivery of materials such as drugs, hormones, or neurotransmitters to living tissue is assuring that the materials are delivered to the target receptor location in the intended amount. Many materials which are delivered to a patient, even though beneficial in the treatment of a specific condition, may be moderately or even strongly noxious or damaging to healthy tissue. It is therefore one object of conventional materials application treatment to maximize dosage to a desired location and to minimize dosage to locations which do not require the delivery of the material. Additionally, newer medical treatments may include procedures which remove unwanted deposits of materials with an expectation that the removal will be assisted by physical removal (by a withdrawal system) or natural bodily function removal (e.g., the circulatory system), or which may attempt to stimulate the body to produce natural chemicals (of which a patient may be deficient) at an increased rate (e.g., electrical stimulation to increase the production of dopamine). Because these procedures are usually highly invasive, it would be extremely desirable to have a real time indication of immediate, transient and persistent effectiveness of the procedure. Where undesired deposits or collections of materials are being dispersed, it would be desirable to visualize the actual movement of materials to assist in collecting them (e.g., through catheters) or tracking them to assure that they are not again depositing or collecting (as in intravenous or cerebrospinal fluid blockage), or moving in segments which are too large and could cause blockage in other parts of the body as they are carried about. Unfortunately, with in vivo delivery of materials, particularly extremely small doses in small volumes delivered by small instrumentation into tissue regions protected by the blood-brain barrier, or the brain-cerebrospinal fluid barrier, or into visually inaccessible areas, it has not been possible to observe real time distribution of the material delivery, or the dispersion or distribution of the material at the injection or infusion site within the tissue. Where even small variations or miscalculations about the location of the target sight and the delivery device can significantly affect the delivery of material and the effectiveness of the delivered material, real time observation of the material delivery is even more critical than in topical or gross (e.g., massive systemic injection) delivery events. There has been no truly effective observation system for such delivery prior to the invention of U.S. Pat. No. 6,026,316, which specification is incorporated herein, in its entirety, by reference.

The basic operation of the U.S. Pat. No. 6,026,316 involves the initial MR imaging observation of a molecular environment of a patient (e.g., a particular area or region of a patient, such as tissue, particularly such tissue as that present in organs or systems of animal bodies and especially the human body, including, but not limited to the intracranial compartment and the various anatomic regions of the brain, including the cerebral ventricles, cisterns, epidural and subdural spaces, sinuses, and blood vessels, the spinal cord, including disks, nerves and associated vascular system, the heart and the coronary vascular circulation, liver and the hepatic vascular circulation, kidney and the renal vascular circulation, spleen and the splenic vascular system, gastrointestinal system, special senses, including the visual system, auditory system, and olfactory system endocrine system including the pituitary gland, thyroid gland, adrenal gland, testes, and ovaries, with observation of an MR image signal intensity at a given time and/or state (e.g., prior to material introduction or at some defined stage of material diffusion into the molecular environment. In an example of the method of the invention, the distribution of the material in the tissue is determined by releasing an amount of the material through a drug delivery device positioned in the tissue, allowing the material to diffuse in the tissue, and analyzing the resulting MR signal intensity. On a continual basis or at some subsequent time interval later (e.g., a pulsed interval, preselected interval, random interval, frequent or sporadic intervals), the MR image of the molecular state within the same general area is observed. Changes in the characteristics, properties or quality of the image, such as the image signal intensity within the area are presumptively (and in most cases definitively) the result of the introduction of material into the original molecular environment and alteration of the MR response for regions of the environment where delivered material concentration has changed. By repeating observation of the MR image signal intensity within an area at least once (e.g., first taking the initial observation at a material concentration state at a time Ti, and at least one subsequent observation of MRI-observable changes such as in the signal intensity qualities at a time T2), the change in MR image signal intensity qualities can be related to the change in material concentration between times T, and T2, whether that change is from a starting point of zero concentration or from an existing concentration level. The observations therefore relate to the actual delivery of material into the molecular environment in an observable, and to some lesser degree, quantifiable manner. The change in the signal, e.g., the change in the amplitude of the MR signal in the visible image may be altered by:

a) a change in the apparent diffusion coefficient (ADC) of tissue water protons;
  b) a change in tissue magnetic susceptibility (BO);
  c) a change in T1 tissue relaxivity (T1);
  d) a change in T2 tissue relativity (T2);
  e) a change in tissue magnetization transfer coefficients (MTC);
  f) a change in tissue chemical shift frequency;
  g) a change in tissue temperature; or
  h) a combination of any one or more of a)–g) alone or with other effects.

The MR signal is dephased by the random motion of diffusing water molecules, and the presence of the delivered material locally affects the degree to which the amplitude of the signal is altered by the dephasing. If the amount of active ingredient to be delivered is quite small, or the effect of that material on the alteration of the amplitude is minimal, the delivered material may be associated with a larger amount of a second material or another more NM signal responsive material, which are preferably selected on a basis of similarity in diffusion rates through like materials or at least comparable (mathematically relatable) diffusion rates. In this manner, using such a taggant material, the diffusion of the delivered material may be assumed to relate to the diffusion/delivery of the taggant material. Unlike other observational techniques, these taggant materials may be readily provided as non-toxic, inexpensive taggant materials since there is such a wide variety of materials which could be so used, and their only functional requirements would be diffusion rate and non-toxicity. Many dyes commonly used in medical procedures could be used for this purpose.

The availability of an MR-visible drug delivery device combined with NM-visible chemical or drug agents would make it possible to obtain near real-time information on drug delivery during inter-ventional procedures in an intraoperative MR system, as well as for pre-operative and post-operative confirmation of the location of the drug delivery device. Medical and surgical applications would include vascular surgery and interventional radiology, cardiac surgery and cardiology, thoracic surgery and radiology, gastrointestinal surgery and radiology, obstetrics, gynecology, urology, orthopedics, neurosurgery and interventional neuroradiology, head and neck surgery and radiology, ENT surgery and radiology, and oncology. In addition to direct tissue injection, the method of the invention applies to drug delivery via intra-luminal, intra-cavitary, laparoscopic, endoscopic, intravenous, intra-arterial applications.

There is currently considerable interest in the therapeutic use of small ions as well as macromolecules in the treatment of various neurologic diseases. To be effective, such molecules must be able to reach target tissue receptors. Many molecules that are used in therapeutic drugs are large in size, for example, neuroleukin, a neuromodulator drug tested for treatment of amyotrophic lateral sclerosis is about 56 kDa, bethanechol chloride used in treatment of Alzheimer's Disease is about 196 kDa and nerve growth factor is about 13 kDa. While the importance of large molecular weight molecules in direct parenchymal drug therapy is growing, little is known about the time course and the spatial range of their actions, since dynamic visualization methods for studying macromolecular diffusion have not been available.

Diffusion of drug and/or water protons in a complex medium, such as a brain cell microenvironment, is influenced by numerous factors. Materials injected into the brain or spinal cord do not move unimpeded through the aggregations of neurons, glia, capillaries, and nerve fibers. The distribution of a drug volume in the brain cell microenvironment following injection directly into brain tissue is governed by a number of factors including the physicochemical characteristics of the drug, capillary uptake, metabolism, excretion, size of the extracellular space (the volume fraction), and geometry of the brain cell microenvironment (tortuosity). The degree to which each of these factors influences the distribution of a particular drug agent within the brain or spinal cord is an important determinant of the effectiveness of drug treatment of diseases of the central nervous system.

Despite the fact that the average spacing between brain cells may be no more than 20 nm, the mean free path of an ion at the typical ionic strength of the mammalian nervous system is only about 0.01 nm. In ways similar to altering the local ADC of the water protons, presence and transport of a drug through a tissue will also alter the magnetic susceptibility, $T1$, $T2$, MTC, water proton diffusion anisotropy, chemical shift frequency, and temperature of the protons within each imaged voxel. This represents the distance traveled between collisions with other molecules. Almost all these collisions actually take place with water molecules since the concentration of water is 55 M. Thus ions intrinsic to the brain rarely encounter cell membranes and generally behave as though they were in a free medium. However, the diffusivity proper-ties becomes much more complicated when the boundary has a complex geometry, or when macromolecular interactions involve exogenous solutions injected into tissues.

A medical device used in the preferred practice of the present invention for delivery of materials may vary widely with respect to its structure, being highly dependent upon the particular procedural use to which it is being intended. However, there are many features which can be common to all of the devices or which should at least be considered in the various constructions. The simplest device could be a single delivery tube (catheter) which has MR responsive material in or on the composition of the tubing 19, preferably near the distal end or outlet of the delivery tube for assisting in detection by the MR imaging system. The next level of simplified construction would be the presence of MR coils or microcoils at or near the distal end of the catheter. This again, as elsewhere described, improves the visibility of the viewable signal observable by the MRI system. More than one coil or microcoil may be present, as the distribution of microcoils along a length of the catheter helps define the region within which local signals are detected at efficient intensities. That is, each coil acts as a detector of local MR intensity, and each coil supports a volume around the coil which is observable by MRI systems. The coils may add or integrate their detectable volumes, defining a combined volume which can be efficiently observed by the MR system. As different medical procedures are performed in different environments, with different shapes and different variations in densities, the coils may be located, sized, angled, or otherwise designed to provide specific MR signals and/or responses tailored to the anticipated needs of a particular procedure. In general, the invention is best practiced by employing an array of RF microcoils, such that an image is obtained for any orientation of the drug delivery device.

The device may also include numerous catheter elements and/or ports and/or supplemental or independent functional elements. For example, at least two ports may be needed, one to carry in on chemical material and another to deliver a second distinct chemical material which is or may become desirable during a medical procedure. For example, in addition to a primary treatment chemistry being delivered, saline solutions or specifically tailored solutions to dilute potential oversized deliveries could be desirable. Some treatments may require sequences of drug delivery or delivery of various drugs which may not be storage stable prior to delivery to a patient. Separate ports would be desirable in those events. Additionally, ports may be used to evacuate undesirable materials which are directly or indirectly introduced by the medical procedure. A withdrawal port may comprise a tube with a port which can be attached to negative pressure with respect to the an opening in such a withdrawal port, thus being able to reduce liquid or small particle solids volumes within the area of the procedure. Where the liquid volume or solids are MR viewable, the MR viewable device may be directed towards specific locations or areas and the ports targeted towards those specific areas. In addition, the various ports may be marked or designed to provide distinct signals when viewed by MR systems so that they may be distinguished during performance of the procedures. For example, MR insensitive materials may be used to line a port or materials with different distributions or intensities of MR response may be used in the various ports to differentiate the elements while being observed during performance of procedures. For example, where a withdrawal tube has openings through which materials may be withdrawn, the orientation of that opening within the device becomes important. By lining the edges of the opening with material having unique MR responsiveness within the device, the position and orientation of the opening can be readily determined. Particularly preferred is a 2,000–5,000 angstrom thick coating of MR-visible material along the distal shaft of the device.

Where multiple catheters or ports or functional elements are combined into a single device, the configuration of the different components should be tailored for a particular procedure. The different components may be associated by various orientations. An MR-visible guidewire may be inserted within the device to assist in positioning the device at a target anatomical location. Particularly preferred is a guidewire or other structural support made of Nitinol™ or other MR-compatible shape memory metal. This is the simplest geometry and provides for smallest diameter sizing of the device. Other configurations such as parallel alignment of the elements in a strip-like orientation, stacking of elements in rows and columns, or mixtures of these and other configurations may also be useful. Other elements which may be included within the device, in addition to or separate from the use of delivery and/or withdrawal tubes, include thermal elements (for providing heat), radiation carrying elements (e.g., ultraviolet radiation, visible radiation, infrared radiation, and even hard radiation carrying elements, such as optical fibers or other internal reflection radiation carrying systems), detection elements (e.g., pH indicators, electronic activity indicators, pressure detectors, ion detectors, thermal detectors, etc.), and any other sensing or detection element which would be useful during medical procedures. These individual elements are each extendable to permit optimal positioning within the tissue would be configured as desired or needed for the particular procedure intended for the device. Procedurally inert elements such as structural supports, reinforcing elements or coatings, back-up elements, and the like, may also be present within the device. Particularly preferred as structural supports or reinforcing elements are circumferential bands of Nitinol or other MR-compatible shape memory metals which, when activated, can facilitate accurate directed placement of the functional tip of the device.

One type of configuration which is presently considered as the preferred embodiment of the invention is the use of a core of element(s) surrounded by a sheath or distribution of additional elements. A central core element my comprise a single tube for delivery of a material, a pair of tubes for delivery of two chemicals, a delivery and withdrawal tube, or a procedurally inert structural support element. Around the central core element may be disposed multiple additional elements, usually seeking as near to a circular distribution about the central core as geometries allow. The attempt at the circular distribution is primarily for purposes of optimizing a small size for the diameter of the article, and is not necessarily a functional aspect to the performance of the device. MR responsive materials, including MR microcoils, may be located within the central core, around the central core (beneath any next layering of elements), or over the elements surrounding the central core. Where one or more of the elements receive, transmit or are powered by electrical signals, it is desirable that these elements be electrically separated by either or both of physical separation or additional insulation to prevent mixing or cross-transmission of signals between the distinct elements. Carrying and withdrawing tubes (as well as other elements) may also secondary functions. For example, a carrying tube may be conductive (by being naturally conductive or by having a conductive coating in or outside of the tube) and the electrical connection may be associated with an electronic element or component at the distal end of the device. The tube may thereby act as a carrying tube and electrical connection to the electronic component or element. Structural or adhesive support materials between different elements may also provide such functions.

The various individual elements within the device must be structurally associated, especially away from the distal end, and during insertion, may need structural association at the distal end. The structural support or structural integrity may be provided by some physical means of attaching the various elements. This may be done by adhesive materials between the individual elements (which adhesive should be MR compatible), fusion of the various elements, or by coextrusion of the tubes into a single unit (or single component of a multiple element device). The adhesive may be an organic or inorganic adhesive. The distal end of the device may have the ends of the elements temporarily or controllably bonded during insertion. This may be beneficial because it may be desirable to have the individual elements fan out or separate during a medical procedure, for example, as in the case of a target tissue or area of pathology which is anatomically extensive. The adhesive could be water soluble (which would dissolve in a timely manner after insertion), solvent soluble (with solvent delivered into the distal end during a preliminary procedure, or radiation disruptable (e.g., a positive-acting resist adhesive composition which is sensitive to UV, visible or IR radiation which may be delivered through a radiation carrying port). Many other variations and combinations of these considerations and constructions may be used within the practice of the present invention. in another embodiment the dialysis probe is replaced by an MR-visible microcatheter, which is a single extrusion catheter made from one of several possible sizes of a polyethylene terephthalate proximal shaft. A 12 mm distal segment of the microcatheter drug delivery device is made of elastomeric hydrogel or similar soft material which minimizes tissue damage during insertion. A plurality of semipermeable membranes are placed circumferentially at regular intervals along the distal segment of the microcatheter, thus enabling wide dispersion of an injected agent, semipermeable membrane consisting of a 0.18–0.22 ml millipore filter. The companion microguidewire in this example is made of Nitinol or similar memory metal which enables directed placement of the tip of the catheter. A microguidewire may be threaded into a clear hub luek-lock cap made of polymethel-pentene or similar MR-compatible plastic. Both the catheter and guidewire have a linearly arranged array of radiopaque and MR-visible markers disposed at the distal end to provide easily identifiable reference points for trackability and localization under MR imaging and Xray fluoroscopy guidance. The microcatheter can also be made from any of the well known soft, biocompatible plastics used in the catheter art such as Percuflex, a trademarked plastic manufactured by Boston Scientific Corporation of Watertown, Massachusetts. When the delivery device is positioned intracranially, the distal markers will be identifiable in an MR image and by X-rays. In another preferred embodiment, two or more R-F microcoils are placed along the distal shaft of the microcatheter.

The delivery device can be employed to deliver pharmacologic therapies in order to reduce morbidity and mortality associated with cerebral ischemia, intracranial vasospasm, subarachnoid hemorrhage, and brain tumors. In the method of the invention the distal tip of the multi-lumen catheter assembly is typically positioned a few millimeters above the intracranial target structure using MR imaging. In one embodiment of the invention, surface modifications of the material components of the dialysis probe enable timed-release kinetics of MR-visible biologic response modifiers, including peptide macromolecules. In another embodiment of the invention, a pump or other infusion or injection device circulates a solution containing a therapeutic drug or an MR-visible contrast agent through the walls of the dialysis fiber into the brain at rates between 0.01 microliter/min to 10 microliter/min. In another preferred embodiment of the invention, pressure ejection techniques well described in the medical literature are used to deliver a predetermined amount of a therapeutic drug agent or MR-visible contrast through one or more of the tubular components of the multi-lumen device. In one specific preferred embodiment of the invention, the catheter is backfilled with the drug or contrast agent, which is functionally connected to a Picospritzer™ (General Valve Corp, Fairfield, N.J.) or a similar instrument that is able to deliver pulses of nitrogen or compressed air with a duration ranging from a few milliseconds to several seconds at a pressure of 10–50 psi. Using such a pressure ejection mode of drug delivery, the concentration of the released substance in the vicinity of the tip is accurately defined by the concentration of the material in the delivery device. A binary solution can also be released, in that two therapeutic or diagnostic compounds can be delivered at the same time by pressure ejection of two materials from two or more separate microcatheters.

Any material delivery system may be used in combination with the multiprobe catheter system of the invention. The material delivery device, for example, may comprise at least one device selected from the group consisting of:

A) a catheter assembly comprising at least two lumens;

B) a catheter assembly of from 2 to 10 mass transporting elements;

C) at least one light carrying element connected to a light reading system so that light projected into said area provides a signal through said light carrying device to said light reading system;

D) a light transmitting element associated with said material delivery device;

E) at least one thermally responsive element connected to a reading system for said thermal response so that temperatures or temperature changes within said area provide a signal to said reading system for said thermal response.

The system may contain an element capable of providing a charge is part of said material delivery device, said charge when provided being at a location on said material delivery device which assists in orienting of ionic material being delivered by said material delivery device within an area electrostatically near a point of release of said material from said material delivery device. The charge providing element may, for example, be present to deliver electrical charge onto said material delivery device electrostatically near a point of release of said material from said material delivery device. The method may include observing the increase of material within aqueous environments or tissue in a living patient comprising the steps of:

a) observing by Magnetic Resonance Imaging a visible image within an area or volume comprising tissue of a living patient, said area or volume including a medical device which can be observed by Magnetic Resonance Imaging, b) causing by said medical device at least some material which causes an alteration in the magnetic response of water in which said material is dispersed or dissolved to increase its concentration within said area or volume comprising an aqueous environment or tissue of a living patient, c) observing a change in a property of said visible image of an area or volume comprising tissue of a living patient while said medical device is still present within said volume, d) observing a change in a property of said visible image after said medical device has been moved from within said area or volume of tissue.

The medical device may stimulate a part of the patient to increase or decrease its production of a chemical whose presence in water causes a change in a property of said visible image. The method may include observing a different rate of passage of a chemical through structural material within the body of a living patient, said structural material having a delivery side and a distribution side, said method comprising the steps of:

a) observing by Magnetic Resonance Imaging a visible image within an area to volume comprising tissue of said living patient, said area or volume including a delivery device which can be observed by Magnetic Resonance Imaging, b) causing by said delivery device to deliver at least some material which causes an alteration in the magnetic response of water in which said material is dispersed or dissolved, c) observing movement of said material within said patient through said material from said delivery side to said distribution side, d) observing a change in a property of a visible image in an area or volume on said distribution side of said material said medical device is still present within said area or volume, and e) observing differences in rates of penetration of said chemical material through said structural material at different areas of said structural material which are indicative of different properties in said structural material at said different areas which are evidence of a clinical condition in said structural material. The changes in property of said visible image of an area or volume may, for example, comprise tissue of a living patient while said material delivery device is still present within said area or volume are caused by at least one change selected from the group consisting of:

a) a change in the apparent diffusion coefficient of tissue water protons;

b) a change in tissue magnetic susceptibility;

c) a change in T, tissue relativity;

d) a change in T2 tissue relativity;

e) a change in tissue magnetization transfer coefficients;

f) a change in tissue chemical shift frequency; and g) a change in tissue temperature.

We claim:

1. A multi-lumen, multi-functional catheter system comprising a plurality of axial lumens, at least one lumen supporting material delivery of primary treatment chemistry to a point of release and a second lumen having a component supporting a functionality electrostatically near the point of release other than material delivery and material removal wherein at least one biological or physiological measuring device is present within at least one lumen in which information from said at least one biological or physiological measuring device is connected to a host computer and said information is received by said host computer, wherein the component provides information other than information from said at least one biological or physiological measuring device and the component is connected to a host computer and said information is received by said host computer.

2. The system of claim 1 wherein said component is also attached to said catheter system.

3. The system of claim 2 wherein the component measures at least one vital sign of a patient.

4. The system of claim 1 wherein material delivery comprises drug delivery.

5. The system of claim 1 wherein material delivery is into tissue.

6. A multi-lumen, multi-functional catheter system comprising a plurality of axial lumens, at least one lumen supporting a functionality other than material delivery and material removal wherein at least one biological or physiological measuring device is present within at least one lumen in which information from said at least one biological or physiological measuring device is connected to a host computer and said information is received by said host computer, wherein a component that provides information other than information from said at least one biological or physiological measuring device is connected to a host computer and said information is received by said host computer, said component is also attached to said catheter system and the component measures a at least one vital sign of a patient, and wherein information from more than one information source is received by the host computer and a treatment planning and control algorithm is present in said host computer to process that information from more than one source.

7. A method of treating a patient according to a treatment plan comprising inserting a catheter system comprising a multi-lumen, multi-functional catheter system comprising a plurality of axial lumens, at least one lumen supporting material delivery of primary treatment chemistry to a point of release and a second lumen having a component supporting a functionality electrostatically near the point of release other than material delivery and material removal a functionally other than material delivery and material removal into a patient, delivering therapy to the patient through the at least one lumen of said catheter system, the therapy comprising material delivery of primary treatment chemistry, taking information of biological or physiological measurements of tissue or fluids within the patient, reporting said information to a computer, and evaluating performance of the treatment plan with the computer based upon comparing said information to expected biological or physiological information.

8. The method of claim 7 wherein information relating to at least two different biological or physiological measurements are electrically transmitted to the computer for evaluating performance of the treatment plan.

9. The method of claim 8 wherein upon evaluation of the performance of the treatment plan as an existing treatment plan, the computer indicates a deviation for a range of acceptable levels of performance of the treatment plan, and an alteration of the existing treatment plan is identified.

10. The method of claim 9 wherein the computer signals the catheter system to actively modify the existing treatment plan.

11. The method of claim 9 wherein the computer signals an operator to actively modify the existing treatment plan.

12. The method of claim 7 wherein upon evaluation of the performance of the treatment plan, the computer indicates a deviation for a range of acceptable levels of performance of the treatment plan, and an alteration of an existing treatment plan is identified.

13. The method of claim 12 wherein the computer signals the catheter system to actively modify the existing treatment plan.

14. The method of claim 9 wherein the computer signals an operator to actively modify the existing treatment plan.

15. The system of claim 7 wherein material delivery comprises drug delivery.

16. The system of claim 7 wherein material delivery is into tissue.

17. A multi-lumen, multi-functional catheter system comprising a plurality of axial lumens, at least one lumen providing material delivery of primary treatment chemistry to a point of release and a second lumen having a component supporting a functionality electrostatically near the point of release other than material delivery and material removal, delivering therapy to the patient through the at least one lumen of said catheter system, the therapy comprising material delivery of primary treatment chemistry, wherein at least one biological or physiological measuring device is present within at least one lumen in which information from said at least one biological or physiological measuring device is connected to a host computer and said information is received by said host computer wherein at least one biological or physiological measuring device is connected to a signal receiving device by an electrical lead associated with the catheter system, the multi-functional catheter system generating a medical response profile using a general purpose computer system wherein said multi-functional catheter system further comprises a central processing unit, dynamic memory, static memory, a display device, input and output devices, mass storage devices, software, user interfaces, and user control devices.

18. The system of claim 17 wherein the computer contains a program with a treatment planning and therapy algorithm tailored to the need of an individual patient.

19. The system of claim 18 wherein said program with a treatment planning and therapy algorithm can be either adaptively adjusted by at least one controller selected from the group consisting of the computer itself as the therapy progresses, monitoring by a remote station and adjusted by health care professionals, and by an automated system at the remote location as the therapy progresses.

20. The system of claim 17 wherein material delivery comprises drug delivery.

21. The system of claim 17 wherein material delivery is into tissue.

* * * * *